United States Patent
Mueller et al.

(10) Patent No.: US 7,326,350 B2
(45) Date of Patent: Feb. 5, 2008

(54) SYSTEM FOR SEPARATING MAGNETICALLY ATTRACTABLE PARTICLES

(75) Inventors: Hans-Juergen Mueller, Bernried (DE); Andreas Holzer, Eichenau (DE)

(73) Assignee: Roche Diagnostics Corporation, Indianapolis, IN (US)

( * ) Notice: Subject to any disclaimer, the term of this patent is extended or adjusted under 35 U.S.C. 154(b) by 521 days.

(21) Appl. No.: 10/484,110

(22) PCT Filed: Jul. 23, 2002

(86) PCT No.: PCT/EP02/08174

§ 371 (c)(1),
(2), (4) Date: Aug. 2, 2004

(87) PCT Pub. No.: WO03/009943

PCT Pub. Date: Feb. 6, 2003

(65) Prior Publication Data

US 2004/0265903 A1 Dec. 30, 2004

(30) Foreign Application Priority Data

Jul. 25, 2001 (DE) ................................ 101 36 060

(51) Int. Cl.
*B03C 1/28* (2006.01)
*B01D 35/06* (2006.01)

(52) U.S. Cl. ...................... 210/695; 210/222; 335/306; 436/526

(58) Field of Classification Search ................ 210/222, 210/695; 335/306; 436/526
See application file for complete search history.

(56) References Cited

U.S. PATENT DOCUMENTS

| 5,827,478 A | 10/1998 | Carey et al. |
| 5,888,835 A | 3/1999 | Bushnell et al. |
| 5,897,783 A | 4/1999 | Howe et al. |
| 5,976,369 A | 11/1999 | Howe et al. |
| 6,033,574 A * | 3/2000 | Siddiqi ........................ 210/695 |
| 6,451,207 B1 * | 9/2002 | Sterman et al. .............. 210/222 |
| 2002/0182751 A1 * | 12/2002 | Herr et al. ................... 436/526 |

FOREIGN PATENT DOCUMENTS

| EP | 0479448 | 4/1992 |
| JP | 620953714 A | 3/1987 |
| WO | WO 96/26011 | 8/1996 |

OTHER PUBLICATIONS

JP Patent Abstract vol. 11, #246 (C-439), Aug. 11, 1987.

* cited by examiner

*Primary Examiner*—David A Reifsnyder
(74) *Attorney, Agent, or Firm*—McDonnell Boehnen Hulbert & Berghoff LLP

(57) ABSTRACT

A system for the separation of magnetically attractable microparticles which are suspended in a liquid, which includes a magnet arrangement having at least two magnets in ring form, the magnet axis of which is oriented perpendicular to the ring plane, and the magnets are arranged above one another in the same direction or in opposite directions, and the ring inner spaces form a space for receiving a vessel. The invention also relates to methods for the separation of microparticles and to a system for the separation and suspension of microparticles in vessels including a magnet arrangement as described above and a vessel holder and a movement device for moving a vessel in the vessel holder in order to obtain a suspension of separated microparticles.

14 Claims, 3 Drawing Sheets a b c

SYSTEM FOR SEPARATING MAGNETICALLY ATTRACTABLE PARTICLES

The present invention deals with the field of analysis, in particular clinical and immunological analysis using magnetically attractable particles.

The invention relates to a system for the separation of magnetically attractable particles which are suspended in a liquid, which includes a magnet arrangement having at least two magnets in ring form, the magnet axis of which is oriented perpendicular to the ring plane, and the magnets are arranged above one another in the same direction or in opposite directions, and the ring inner spaces form a receiving position for a vessel. The invention also relates to methods for the separation and washing of magnetically attractable particles using a system of this type, and to a system which has a movement device for suspending separated particles.

The use of magnetically attractable particles has already been an established principle in the field of chemical analysis for some time. The magnetically attractable particles are used primarily to separate substances/particles which are to be detected out of the sample matrix. For this purpose, the magnetically attractable particles are coated in such a way that they bond to the surface of the material which is to be detected, either directly or after reaction with auxiliary substances. In these processes, it is desired or even necessary for substance which is to be detected to be separated as completely as possible from the sample matrix, so that subsequent analytical steps are not interfered with. It is particularly important to separate the magnetically attractable particles from the sample matrix, in order to allow the particles to be washed and thereby to achieve even further separation of the sample matrix.

Documents U.S. Pat. No. 5,827,478 and U.S. Pat. No. 5,888,835 describe arrangements in which magnetic particles which are in suspension are separated by guiding magnets onto an outer side of a vessel. Supernatant sample liquid is removed from the vessel, and the particles are washed with a cleaning liquid. For this purpose, the particles can be suspended in a washing liquid after the supernatant has been separated off.

Documents U.S. Pat. No. 5,976,369 and U.S. Pat. No. 5,897,783 describe arrangements in which magnetic particles are deposited on the inner wall of a vessel by means of a magnetic dipole. The shape of the magnetic yoke results in separation in which the particles are deposited substantially in the form of a ring. However, when using a dipole of this type, it is not possible to form a homogeneous ring.

Furthermore, EP 0 479 448 has disclosed a separation device which includes a magnet plate with bores, into which vessels containing suspended magnetic particles are introduced. The magnet plate is such that the north-south axis is arranged parallel to the axis of the bore.

In the context of the present invention, it has been found that, although separation arrangements as described in the abovementioned documents do in principle allow sufficient separation, they are in need of improvement with regard to their washing efficiency. Inter alia, it has been found that a very strong, concentrated deposition of particles may very well be disadvantageous, since the particles are very densely packed and therefore clusters which are still densely packed often remain even after a resuspension step. In these cases, the space between the particles is not accessible or is only insufficiently accessible to washing liquids. A further drawback of an intensive, concentrated deposition of particles consists in the fact that resuspension of the particles is often only possible with considerable outlay. The invention proposes a system in which the particles are deposited as uniformly as possible over a relatively large inner surface of a vessel. In this state, both efficient washing or mixing of the particles with a reaction liquid and relatively simple resuspension of the particles are possible. In the case of the system and method according to the invention, the advantageous deposition mentioned here is achieved by an arrangement of at least two magnets in ring form, the magnet axis of which is oriented perpendicular to the ring plane, and the magnets are arranged above one another in the same direction or opposite directions, so that the ring inner space formed forms a suitable location for magnetic deposition.

In the context of the present invention, magnetically attractable particles are both paramagnetic and also preferably ferromagnetic particles. In the case of the ferromagnetic particles, magnetically hard substances, which do not have any residual magnetism or have only a slight residual magnetism after an external magnetic field has been removed, are preferred. Any residual magnetism would make complete resuspension of the particles more difficult. Magnetically attractable microparticles for use in analysis typically have a diameter in the range of a few micrometers, preferably in the range from 1.5-4 µm. Particles of this type are commercially available, for example from Dynal. To be used in analysis contexts, the particles are generally coated with bonding partners. These may be both coatings which directly bond an analyte which is to be detected and also universal coatings, such as for example streptavidin. Specifically bonding microparticles can be generated by reacting universally coated particles with conjugates from a bonding partner for the universal coating (for example biotin) and a bonding partner for the analyte. Since processes for producing microparticles for chemical/immunological analysis are well known in the prior art, they do not need to be explained in further detail at this point.

To carry out an analysis, the microparticles are mixed with a sample liquid, such as blood or serum, so that analytes which are to be detected can bond to the surface of the microparticles or can cause a specific reaction there. Both microparticles and sample liquid can be subjected to other operational steps, such as suspension, dilution, digestion, etc., prior to the reaction step described. To carry out an analysis, it is generally necessary for that part of the sample which does not represent analyte (sample matrix) to be separated off as completely as possible, in order not to interfere with subsequent detection reactions. In the context of the invention, this is achieved by separating the magnetically attractable particles and separating off the liquid which remains (generally also known as supernatant). In general, the separated microparticles must first be washed before further analysis steps are carried out, in order to remove adhering liquid which still also contains sample matrix. According to the invention, a washing step of this type may take place both while the particles are deposited and also by suspending the particles in liquid or while the particles are suspended in liquid. As has already been explained above, the present invention is distinguished by the fact that the microparticles are deposited in a form from which they can be resuspended particularly successfully without any relatively large aggregates being retained. The particles can then be used for analysis in a very wide range of ways.

To carry out a separation, a suspension of magnetic microparticles has to be introduced into the active field of the magnet arrangement, i.e. in the present case into the inner space of the magnets in ring form. This can be achieved primarily by a nonmagnetic vessel in which the suspension is located being introduced into the ring inner space formed by the magnets in ring form. Alternatively, it is also possible for the magnet arrangement to be moved in such a way that the vessel holding the suspension penetrates into the inner space. A further option consists in selecting a magnet arrangement which is composed of two or more parts, preferably two half-shells, which are moved apart in order for a vessel to be introduced, then the vessel is moved into the inner space formed and the parts are moved together in order to apply the magnetic field.

The magnets in ring form in a magnet arrangement according to the invention may be arranged above one another in the same direction or in opposite directions. Orienting the magnets in opposite directions leads to stronger magnetic field gradients and therefore to more rapid separation of particles. However, as has already been explained above, although a reduction in the separation time is in principle advantageous, in order to reduce the time required for the analysis process, it is often also associated with a particle cake which is more difficult to resuspend. If an arrangement with magnets arranged in opposite directions is selected, it is advantageous to provide a holding device which holds the magnets together counter to the repulsion forces. Both in the case of magnets oriented in the same direction and in the case of magnets oriented in opposite directions, it is possible to provide spacers which consist of nonmagnetic material between the individual magnets. The intensity and spatial distribution of the magnetic field can be modified in a relatively simple way by selection of the spacers, in particular their thickness. Consequently, it is easily possible to adapt the magnet arrangement to the particular requirements.

For the field of the invention, it has been discovered that the ring inner space, into which a vessel is introduced for separation purposes, should preferably have a cross section in the range between 4 and 10 mm. Furthermore, it is advantageous if the individual magnets used for the magnet arrangement have a magnetic remanance of greater than 0.8 T. Ring magnets of this type can be obtained, for example, from Bomatec, Höri in Switzerland. In the context of the invention, magnets in circular ring form are preferred, since they are able to achieve homogeneous separation of the particles at the vessel inner wall. However, in principle it is also possible to use magnets with other magnets which are in the form of a closed ring, for example in the form of a square or a polygon. The ring inner space and vessel outer surface are preferably matched to one another in such a way that a gap of preferably 0 to 1.5 mm, better still less than 0.5 mm, remains between the magnet inner wall and vessel outer wall when the vessel in question has been introduced concentrically into the ring magnets.

The present invention has also discovered a device for the resuspension of deposited microparticles which can advantageously be used in a system for separation with a magnet arrangement according to the invention.

The device for suspending deposited microparticles has a vessel holder for holding a vessel. The vessel holder is moved by a movement device in order to suspend particles. It is preferable for the vessel holder to be mounted in such a way that it can be moved in a manner in which the vessel axis is tilted with respect to the vertical. Mounting of this nature can be achieved, for example, by a vessel holder with an outer surface in the form of a segment of a sphere, which is held in a corresponding cavity which has a recess in the form of part of a sphere. The vessel holder can be moved by mechanical connection to an eccentric drive.

The present invention is explained in more detail with reference to figures.

Figure 3:
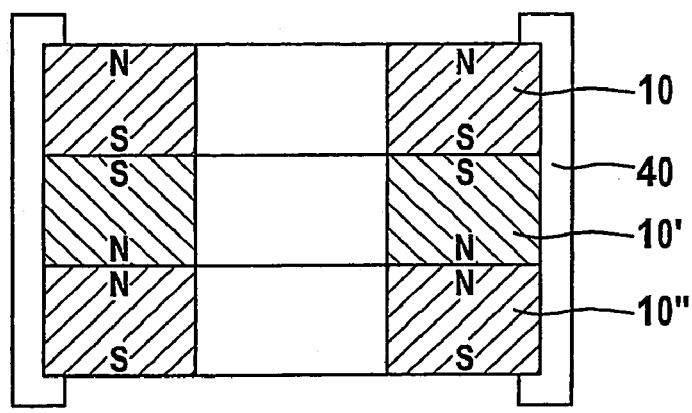
Figure 3:
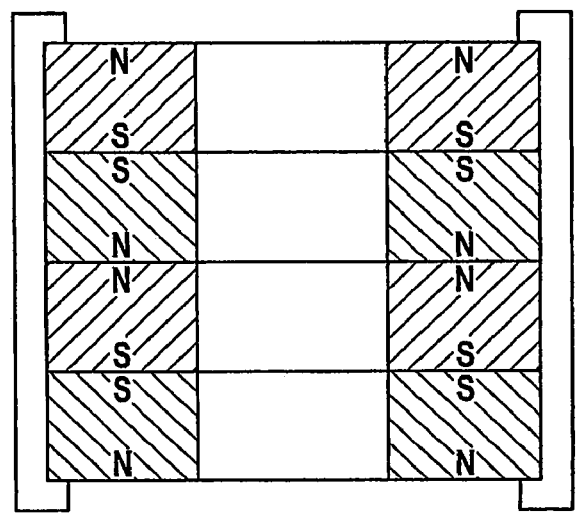
Figure 3:
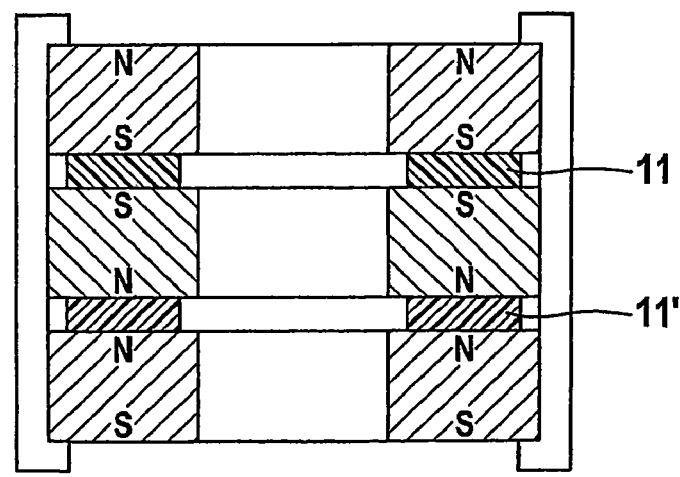

FIG. 3 diagrammatically depicts a cross section through magnet arrangements

Figure 4:
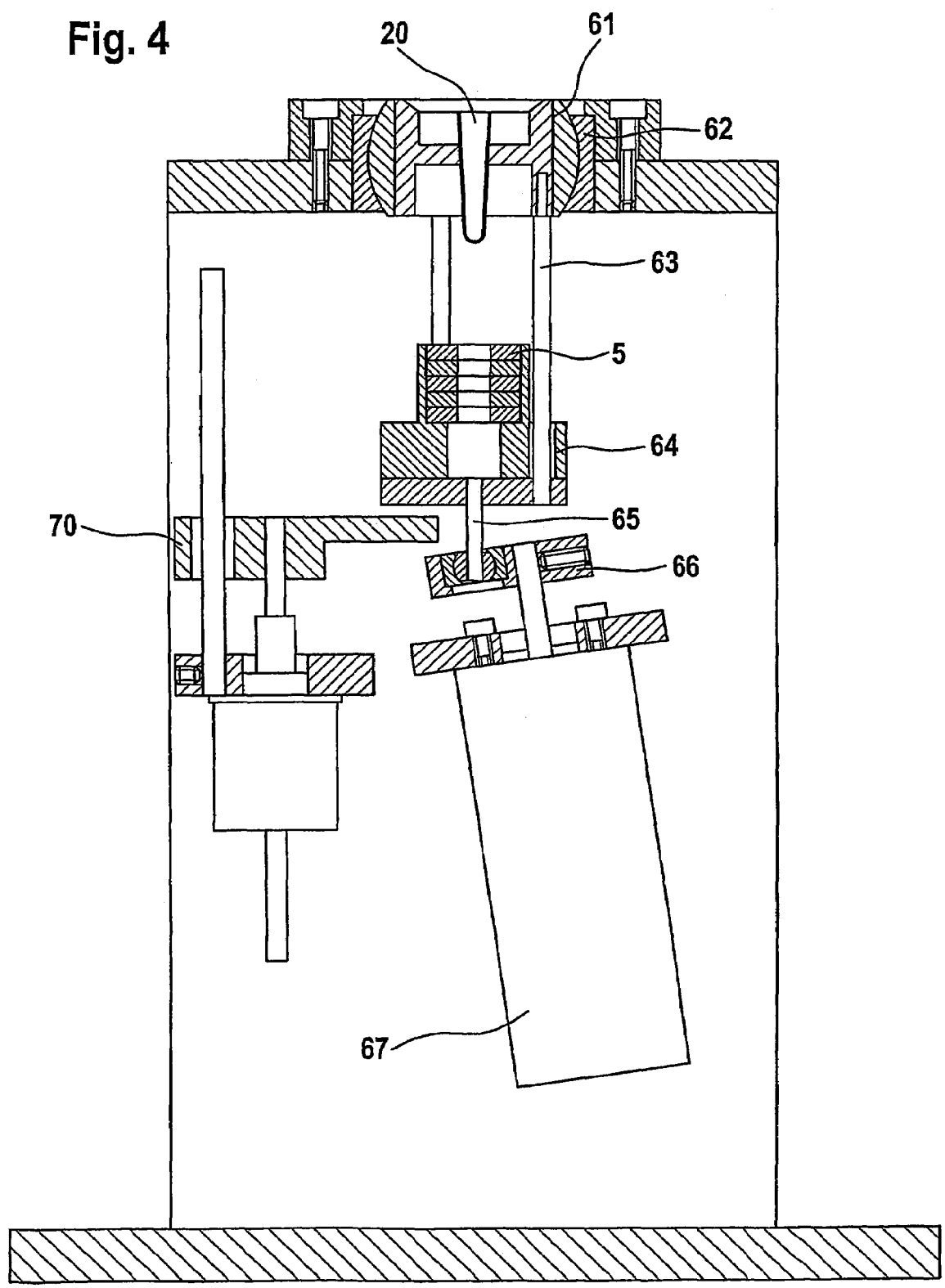

FIG. 4 shows a module for the separation and resuspension of microparticles.

Figure 1:
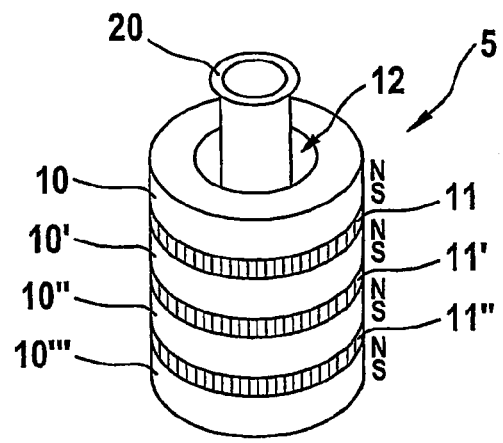
FIG. 1 shows a perspective view of a magnet arrangement

FIG. 1 shows a perspective illustration of a magnet arrangement according to the invention in which four ring magnets (10, 10', 10'', 10''') are arranged above one another. The magnet axis of the ring magnets is designed to be perpendicular to the ring plane. Spacers (11, 11', 11'') are located between the ring magnets. The spacers consist of a nonmagnetic material, for example a plastic. The inner spaces of the ring magnets arranged above one another form an inner space (12) for receiving a sample vessel (20). In the arrangement illustrated, the ring magnets are arranged in the same direction, so that their north-south axes face in the same direction.

Figure 2:
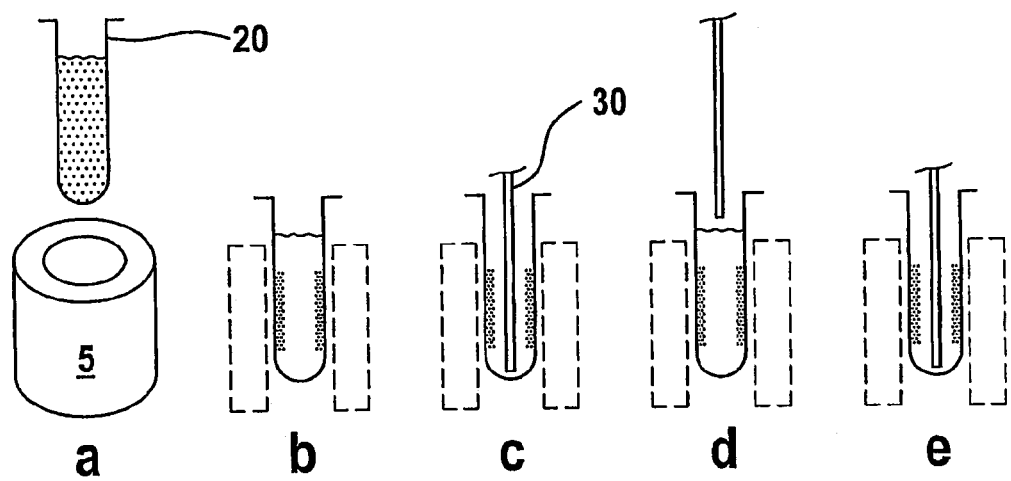
FIG. 2 shows method steps involved in washing microparticles using the magnet arrangement illustrated in FIG. 1
Figure 2:
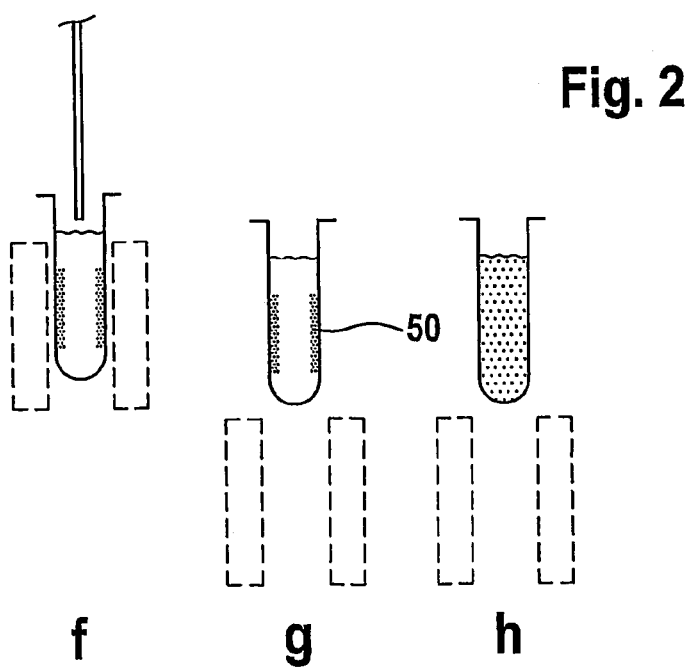

FIG. 2 diagrammatically depicts the individual method steps involved in washing microparticles with the aid of the magnet arrangement illustrated in FIG. 1. FIG. 1a shows a perspective illustration of the magnet arrangement, while the other figures are cross-sectional drawings.

First of all, a vessel with microparticles suspended in it is introduced into the receiving space (12) of the magnet arrangement (5) (FIGS. a and b). As soon as the microparticles have been deposited on the inner wall of the vessel by the magnetic field, the liquid, which is now separate from the microparticles in the vessel, is removed using a pipette (30) (Figure c). Then, washing liquid is added (Figure d), and this in turn is removed from the vessel using a pipette (Figure e). The vessel is filled again with washing liquid (Figure f), and vessel and magnet arrangement are spatially separated from one another (Figure g). Then, the deposited cake (50) of microparticles is suspended in the liquid by moving the vessel (Figure h). As an alternative to the method illustrated, it is also possible to use the introduction of liquid to resuspend deposited microparticles, but this also requires the influence of the magnetic field to have been removed beforehand. The process illustrated in steps a to h can be repeated if necessary. Furthermore, to increase the washing efficiency it is possible to follow step f with step c using fresh washing liquid. The sequence c to f can be repeated as often as desired/necessary.

FIG. 3 shows three different magnet arrangements. FIG. 3a illustrates an arrangement in which three ring magnets of opposite polarities are held together by a clamp (40). FIG. 3b illustrates a corresponding arrangement with four ring magnets arranged in opposite directions. Finally, FIG. 3c shows an arrangement in which spacers (11, 11') are located between the ring magnets.

FIG. 4 shows a system which is suitable both for the magnetic separation of microparticles and for the resuspension of deposited microparticles in liquids. In this arrangement, a vessel is located in a holder (61), the outer shape of which corresponds to part of a sphere. The part of a sphere is held in a stationary die (62) matched to the holder. The holder is arranged in the die in such a way that a movement which tilts the longitudinal axis of the vessel with respect to the vertical can take place. For this purpose, the holder has connecting rods (63) which are connected to a movement plate (64). On its underside, the movement plate likewise has a connecting rod (65), which is set in tumbling motion by an eccentric disk (66). For this purpose, the eccentric disk

(66) is set in rotation by means of a motor (67). Furthermore, a magnet arrangement (5) as shown in FIG. 1 is arranged on the movement plate (64). The movement plate can be moved upward along the connecting rods (63) by means of a lifting device (70), so that the vessel moves into the inner space formed by the magnets. This arrangement can be used firstly to carry out a separation process, in which a vessel is moved into the receiving position and the magnet arrangement (5) is already arranged in such a way that a lower region of the vessel projects into its inner space, or alternatively the magnet arrangement can be moved upward by means of the lifting device (70) in order to effect separation of particles. Steps b to f illustrated in FIG. 2 can then be carried out in this position. For the resuspension, the magnet arrangement (5) is moved into its lower position, illustrated in FIG. 4, and the vessel with its contents is set in motion by the eccentric arrangement, so that the microparticles are resuspended.

The invention claimed is:

1. A system for the separation of magnetically attractable microparticles which are suspended in a liquid, which includes
    a magnet arrangement having at least two magnets, each having the shape of a ring, a magnet axis of which is oriented perpendicular to a ring plane, and the magnets are arranged above one another such that their polarity is in opposite directions and the magnets are held together against magnetic repulsion forces by a holding device, and ring inner spaces form a space for receiving a vessel.

2. The system as claimed in claim 1, in which spacers made from nonmagnetic material are located between the magnets having the shape of a ring.

3. The system as claimed in claim 1, in which the ring inner space of the magnets has a cross section in the range of 4 mm and 10 mm.

4. The system as claimed in claim 1 or 3, in which the individual magnets have a magnetic remanence greater than 0.8 tesla.

5. The system as claimed in claim 1, which includes the vessel for holding a suspension of microparticles.

6. The system as claimed in claim 5, in which the suspended microparticles are coated with an immunological bonding partner.

7. The system as claimed in claim 6, in which the magnetic microparticles have a mean diameter in the range from 1.5 to 4 µm.

8. A method for separation of magnetic microparticles, in which a vessel having a suspension of microparticles is introduced into the receiving position of a system for the separation of magnetically attractable microparticles which are suspended in a liquid, which includes a magnet arrangement having at least two magnets, each having the shape of a ring, a magnet axis of which is oriented perpendicular to a ring plane, and the magnets are arranged above one another such that their polarity is in opposite directions and the magnets are held together against magnetic repulsion forces by a holding device, and ring inner spaces form a space for receiving the vessel, so that the microparticles are deposited on an inner wall of the vessel and a first liquid remains.

9. The method as claimed in claim 8, in which, after the microparticles are deposited on the inner wall of the vessel, the first liquid is removed, the action of the magnetic field is eliminated, a second liquid is added and the microparticles are suspended in the second liquid.

10. The method as claimed in claim 9, in which, after the suspending step, the microparticles are deposited again.

11. The method as claimed in claim 8, in which, after the microparticles have been deposited at the inner wall of the vessel, a second liquid is added, while the microparticles remain on the vessel inner wall and the second liquid is removed.

12. A system for the separation and suspension of microparticles in vessels including a magnet arrangement having at least two magnets, each having the shape of a ring, a magnet axis of which is oriented perpendicular to a ring plane, and the magnets are arranged above one another such that their polarity is in opposite directions and the magnets are held together against magnetic repulsion forces by a holding device, and ring inner spaces form a space for receiving a vessel, and
    a vessel holder and a movement device for moving a vessel in the vessel holder in order to obtain a suspension of separated microparticles.

13. The system as claimed in claim 12, in which the vessel for the separation and resuspension remains in the same position and the magnet arrangement can be moved, by a device, out of a separation position into a suspension position, in which the action of the magnet arrangement on the contents of the vessel is so slight that the microparticles can be suspended.

14. The system as claimed in claim 12, in which the movement device comprises an eccentric arrangement.

* * * * *

UNITED STATES PATENT AND TRADEMARK OFFICE
CERTIFICATE OF CORRECTION

PATENT NO. : 7,326,350 B2  
APPLICATION NO. : 10/484110  
DATED : February 5, 2008  
INVENTOR(S) : Hans-Juergen Mueller and Andreas Holzer Page 1 of 1

It is certified that error appears in the above-identified patent and that said Letters Patent is hereby corrected as shown below:

Title page, item 73, Assignee:

delete "Roche Diagnostics Corporation"

replace with -- Roche Diagnostics Operations, Inc. --

Signed and Sealed this

Twenty-seventh Day of January, 2009

JOHN DOLL  
*Acting Director of the United States Patent and Trademark Office*